US00PP31838P2

(12) United States Plant Patent
Ashton

(10) Patent No.: US PP31,838 P2
(45) Date of Patent: Jun. 2, 2020

(54) ***ROSMARINUS* PLANT NAMED 'LOWROS12'**

(50) Latin Name: *Rosmarinus officinalis*
Varietal Denomination: Lowros12

(71) Applicant: Lowaters Ltd., Hampshire (GB)

(72) Inventor: Ian Ashton, Hampshire (GB)

(73) Assignee: LOWATERS LTD., Hampshire (GB)

( * ) Notice: Subject to any disclaimer, the term of this patent is extended or adjusted under 35 U.S.C. 154(b) by 0 days.

(21) Appl. No.: 16/501,792

(22) Filed: Jun. 7, 2019

(51) Int. Cl.
*A01H 5/02* (2018.01)
*A01H 6/50* (2018.01)

(52) U.S. Cl.
USPC ..... Plt./258

(58) Field of Classification Search
USPC ..... Plt./258, 226
CPC ... A01H 5/02; A01H 5/12; A01H 5/00; A01H 6/50
See application file for complete search history.

*Primary Examiner* — June Hwu
(74) *Attorney, Agent, or Firm* — Penny J. Aguirre

(57) ABSTRACT

A new cultivar of *Rosmarinus* plant named 'Lowros12' that is characterized by its arching stems, its aromatic foliage, its large bright blue flowers in spring that are spread apart from each other on the stem, and its floriferous blooming habit.

2 Drawing Sheets

Botanical classification: *Rosmarinus officinalis.*
Variety denomination: 'Lowros12'.

BACKGROUND OF THE INVENTION

The present invention relates to a new and distinct cultivar of *Rosmarinus officinalis* and will be referred to hereafter by its cultivar name, 'Lowros12'. 'Lowros12' is an evergreen shrub grown for landscape, container, and culinary use.

The new *Rosmarinus* arose from a breeding program conducted by the Inventor at a nursery in Southampton, Hampshire, United Kingdom. The objective of the breeding program was to develop a new *Rosmarinus* cultivar with an abundance of flowers.

The new *Rosmarinus* originated from open pollination of *Rosmarinus officinalis* 'Fox Tail' (not patented) in 2009. The male parent is therefore unknown. 'Lowros12' was selected as a unique single plant from the progeny resulting seedlings in 2012.

Asexual propagation of the new cultivar was first accomplished by the inventor by stem cuttings in March of 2017 in Southampton, Hampshire, United Kingdom. Asexual propagation by stem cuttings has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Lowros12' as a unique cultivar of *Rosmarinus.*

1. 'Lowros12' exhibits arching stems.
2. 'Lowros12' exhibits aromatic foliage.
3. 'Lowros12' exhibits large bright blue flowers in spring that are spread apart from each other on the stem.
4. 'Lowros12' exhibits a floriferous blooming habit.

The female parent, 'Fox Tail', is similar to 'Lowros12' in having arching stems. 'Fox Tail' differs from 'Lowros12' in having shorter stem internodes. 'Lowros12' can also be compared to the *Rosmarinus* cultivar 'Blue Rain' (not patented). 'Blue Rain' is similar to 'Lowros12' in having arching stems. 'Blue Rain' differs from 'Lowros12' in having flowers that are duller blue in color and in having a less floriferous blooming habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of a 3-year-old plant of the new *Rosmarinus* as grown in a 21-cm container in Southampton, Hampshire, United Kingdom.

The photograph in FIG. 1 provides a side view of 'Lowros12' in bloom.

Figure 1:
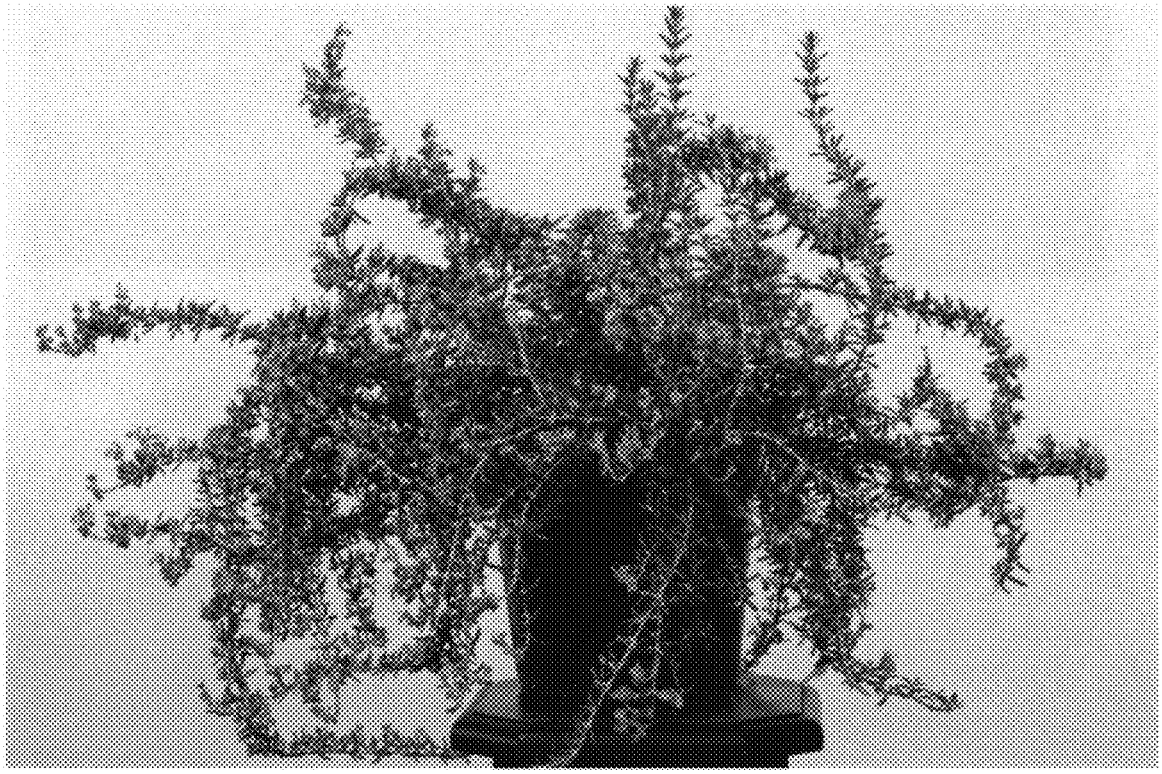
Figure 2:
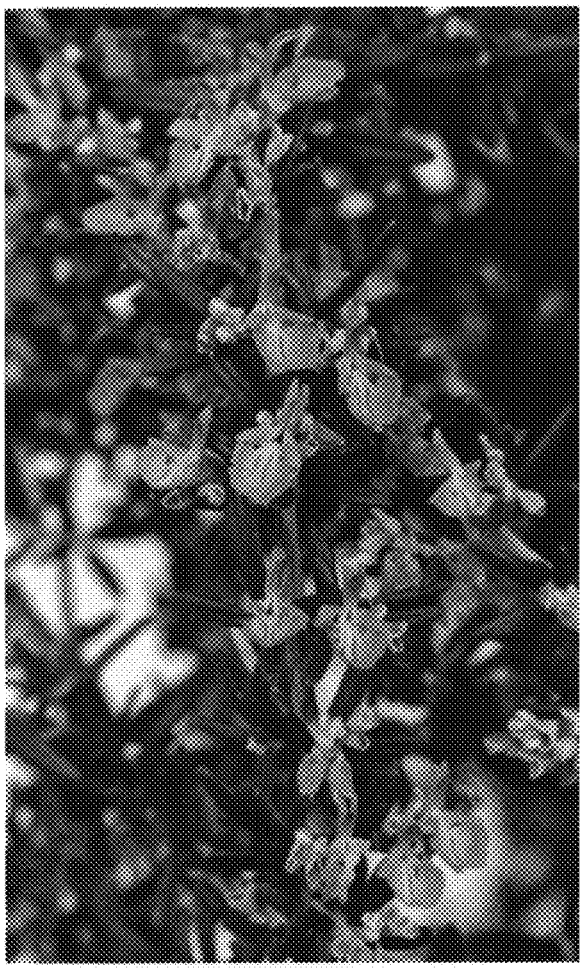

The photograph in FIG. 2 provides a close-up view of flowering stem 'Lowros12'.

Figure 3:
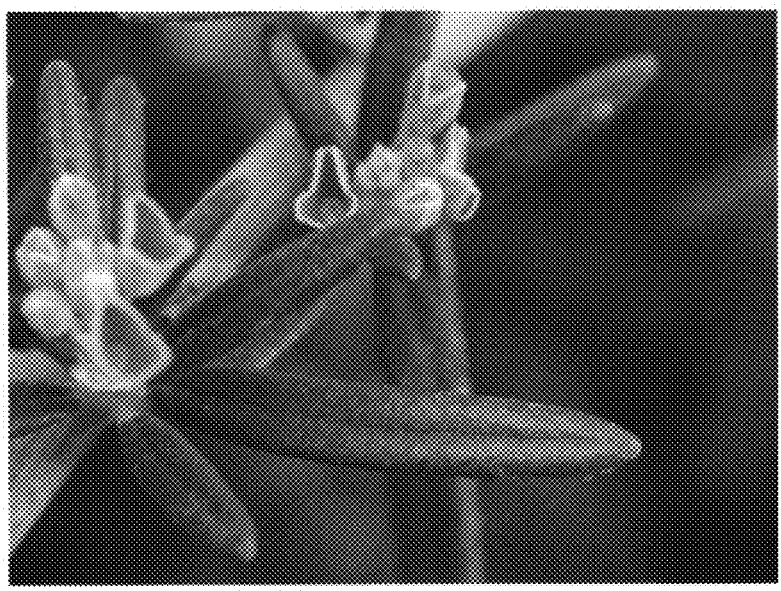

The photograph in FIG. 3 provides a close-up view of the foliage of 'Lowros12'.

The colors in the photographs may differ slightly from the color values cited in the detailed botanical description, which accurately describe the colors of the new *Rosmarinus*

DETAILED BOTANICAL DESCRIPTION

The following is a detailed description of the new cultivar of 3-year-old plants of the new *Rosmarinus* as grown in 21-cm containers Southampton, Hampshire, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Spring in Southampton, Hampshire, United Kingdom.

*Plant type*.—Evergreen shrub (herb).

*Plant habit*.—Spreading with arching stems.

*Plant size*.—Reaches about 40 cm in height and spread as a 3-year-old plant grown in a container.

*Hardiness*.—At least in U.S.D.A. Zones 7 to 11.

*Diseases and pests*.—No susceptibility or resistance to diseases or pests has been observed.

*Root description*.—Fibrous, 161A in color.

*Propagation*.—Stem cuttings of soft new growth.

*Growth rate*.—Moderate to high.

*Root development*.—4 to 8 weeks for cuttings taken from soft new growth in second half of the year, a pinched plug will produce a P9 liner in 10 to 12 weeks in late spring and summer.

Stem description:

*Shape*.—Rounded to slightly quadrangular.

*Stem color*.—New growth; 145B, mature stems (including internodes); 200D, bark; 199B to 199D.

*Stem size*.—Main stems; an average of 26 cm in length and 2 mm in diameter, lateral branches; average of 8 cm in length and 2 mm in diameter.

*Stem aspect*.—Pointed in all directions and strongly arching to curled.

*Stem strength*.—Strong.

*Stem surface*.—New growth and mature stems; dull and densely woolly pubescence; 157B in color on young stems and 156C in color on mature stems, bark; finely barked.

*Internode length*.—Average of 1.4 cm.

*Branching*.—Average of 10 main stems, an average of 13 lateral branches per main stem.

Foliage description:

*Leaf shape*.—Linear to narrow oblong.

*Leaf division*.—Simple.

*Leaf base*.—Attenuate.

*Leaf apex*.—Bluntly acute.

*Leaf fragrance*.—Strongly aromatic, rosemary scented.

*Leaf venation*.—Anastomosing, 137B in color on upper surface, 157B in color on lower surface.

*Leaf margins*.—Entire, revolute.

*Leaf arrangement*.—Opposite.

*Leaf attachment*.—Short petiolate.

*Leaf surface*.—Upper surface; smooth, glabrous and moderately glossy, lower surface; matte, dense covered with woolly pubescence; 0.2 mm in length and 157C to 157D in color.

*Leaf size*.—Average of 2.2 cm in length and 4 mm in width.

*Leaf color*.—Young leaves; upper surface NN137A, lower surface 157D, mature leaves; upper surface 137B, lower surface 157B to 157C.

*Petioles*.—Average of 1.5 mm in length and 1 mm in width, 145D in color, surface; smooth, glabrous and matte, strong.

Inflorescence description:

*Inflorescence type*.—Axillary and terminal raceme.

*Lastingness of inflorescence*.—Individual flowers last about 7 days, self-cleaning.

*Inflorescence size*.—An average of 3.5 cm in length and 2.3 cm in width.

*Flower type*.—Labiate.

*Flower number*.—An average of 14 flowers per inflorescence and 20,000 per plant.

*Flower fragrance*.—None.

*Flower aspect*.—Outward.

*Flower buds*.—Flattened obovate in shape, about 7 mm in length and 3 mm in diameter, petal portion 91A and 91B in color, calyx portion 138B and 138C in color, surface; petal portion very sparsely pubescent with hairs 0.3 mm in length and too small to measure with color chart with calyx portion moderately pubescent with hairs 0.2 mm in length and too small to measure with color chart.

*Flower size*.—Average of 1.4 cm in length, 8 mm in diameter, and 1.3 cm in depth.

*Peduncle*.—An average of 2.2 cm in length and 1 mm in width, moderately strong, aspect; terminal inflorescences an average angle of 0° to lateral stems, axillary inflorescences in an average angle of 45° to lateral stems, 145C in color, surface matte and moderately to densely covered with very short glandular hairs; 0.3 mm in length and 157D in color.

*Pedicels*.—Average of 3.5 mm in length and 0.5 mm in width, color in between 147A and 197A but slightly darker, surface matte and moderately covered with very short glandular hairs; average 0.3 mm in length and 157D in color, moderately strong, held at an average angle of 30° to peduncle.

*Calyx*.—Two-lipped with lower lip cleft, about 4 mm in length and 2.5 mm in width.

*Sepals*.—2, lower 75% fused, 4 mm in length, upper sepal 1.5 mm in diameter, lower sepal 2 mm in diameter, apex acute, entire margin, narrow obovate in shape, 138A and 138B in color on both surfaces, upper surface smooth, glabrous and matte, lower surface matte and moderately pubescent with very short glandular hairs; 0.2 mm in length too small to measure with color chart.

*Petals*.—5, fused into one upper petal (2 fused upper petals), two lateral petals and one lower petal, upper petal; oblong in shape, apex cleft, 6 mm in length and 3 mm in width, color when opening 90D veined 90A to 90B on upper surface and a color between 91A and 91B on lower surface, color when fully open 90C to 90D veined 90B on upper surface and a color between 92A and 92B on lower surface, lateral petal; apex obtuse, oblong in shape, 4 mm in length and 1.5 mm in width, color when opening 90D veined 90A to 90B on upper surface and a color between 91A and 91B on lower surface, color when fully open 94D slightly spotted with 94B on upper surface and 93D on lower surface, lower petal; reniform in shape, apex broad emarginate, 7 mm in length and width, color when opening 91A and slightly spotted with 92A on upper surface and a color between 91A and 91B on lower surface, color when fully open 94D slightly spotted with 94B on upper surface with center NN155C and 93D on lower surface, margins entire and moderately undulate on all petals, surface;

all petals smooth and glabrous on upper surfaces, lower surface smooth, glabrous and matte on upper and lateral petals and smooth and matte and very sparsely pubescent with hairs 0.3 mm in length and too sparse to measure color with color chart on lower petal, throat; an average of 1 mm in diameter, smooth and glabrous surface and NN155C in color, tube; an average of 4 mm in length and 1.5 mm in diameter, both surfaces smooth and glabrous and NN155C in color.

Reproductive organs:

*Gynoecium*.—Pistil; 1, average of 1.6 cm in length, style; 1.6 cm in length and 93A in color changing at base to 84D, stigma; linear and pointed in shape, 0.2 mm in width, and 93A in color, ovary; 143A in color.

*Androecium*.—Stamens; 2, filaments; 92B in color and an average of 9 mm in length, anthers; short oblong in shape, average of 1 mm in length and 0.5 mm in width, N92C in color and basifixed, pollen is low to moderate in quantity and 122C in color.

*Fruit and seed*.—None observed to date.

It is claimed:

1. A new and distinct cultivar of *Rosmarinus* plant named 'Lowros12' as herein illustrated and described.

* * * * *